(12) United States Patent
Chanda et al.

(10) Patent No.: US 10,172,413 B2
(45) Date of Patent: Jan. 8, 2019

(54) CUSTOMIZED INSOLES FOR DIABETIC AND PRESSURE ULCERS

(71) Applicant: The Board of Trustees of the University of Alabama, Tuscaloosa, AL (US)

(72) Inventors: Arnab Chanda, Tuscaloosa, AL (US); Vinu Unnikrishnan, Tuscaloosa, AL (US)

(73) Assignee: The Board of Trustees of the University of Alabama, Tuscaloosa, AL (US)

( * ) Notice: Subject to any disclaimer, the term of this patent is extended or adjusted under 35 U.S.C. 154(b) by 0 days.

(21) Appl. No.: 15/646,046

(22) Filed: Jul. 10, 2017

(65) Prior Publication Data

US 2018/0008000 A1 Jan. 11, 2018

Related U.S. Application Data

(60) Provisional application No. 62/360,773, filed on Jul. 11, 2016.

(51) Int. Cl.
*A43B 17/00* (2006.01)
*A43B 7/14* (2006.01)
(Continued)

(52) U.S. Cl.
CPC ............ *A43B 7/147* (2013.01); *A43B 1/0045* (2013.01); *A43B 7/141* (2013.01); *A43B 7/142* (2013.01);
(Continued)

(58) Field of Classification Search
CPC ..... A43B 7/1485; A43B 7/1475; A43B 7/148; A43B 17/003
(Continued)

(56) References Cited

U.S. PATENT DOCUMENTS

| 4,651,445 | A | * | 3/1987 | Hannibal | ............. | A43B 13/187 |
| | | | | | | 36/103 |
| 5,555,584 | A | * | 9/1996 | Moore, III | ............... | A43B 7/28 |
| | | | | | | 12/142 N |

(Continued)

OTHER PUBLICATIONS

E. Melissa, "Markets for Advanced Wound Management Technologies," 2014.
(Continued)

*Primary Examiner* — Marie D Bays
(74) *Attorney, Agent, or Firm* — Meunier Carlin & Curfman LLC

(57) ABSTRACT

Disclosed herein are insoles useful for treating skin injuries on a foot, for instance ulcers. The insoles are customizable for each patient's foot and can include various portions of differing softness, depending on the needs of the patient. For instance, it can be beneficial for certain sections of the foot to contact a firmer material, whereas other sections contact a softer material. Some, or all, of the materials can include one or more biofidelic skin simulant materials. Thus, various implementations include one or more regions that can include the same or different materials. For example, a custom insole can include a heel support region, a midfoot support region, and a forefoot support region, and the support regions can be subdivided into medial and lateral support regions or toe regions. One or more regions may have a custom isolation segment to prevent the progression of ulcers and/or expedite wound healing.

22 Claims, 10 Drawing Sheets

(51) Int. Cl.
*A43B 1/00* (2006.01)
*A43B 17/10* (2006.01)
*A61F 13/06* (2006.01)
*B29D 35/02* (2010.01)
*B29D 35/12* (2010.01)
*B33Y 10/00* (2015.01)

(52) U.S. Cl.
CPC .............. *A43B 7/143* (2013.01); *A43B 7/144* (2013.01); *A43B 7/148* (2013.01); *A43B 7/1425* (2013.01); *A43B 7/1445* (2013.01); *A43B 7/1475* (2013.01); *A43B 7/1485* (2013.01); *A43B 17/003* (2013.01); *A43B 17/006* (2013.01); *A43B 17/10* (2013.01); *A61F 13/067* (2013.01); *A61F 13/069* (2013.01); *B29D 35/02* (2013.01); *B29D 35/122* (2013.01); *B33Y 10/00* (2014.12)

(58) Field of Classification Search
USPC .................................................. 36/43, 44, 71
See application file for complete search history.

(56) References Cited

U.S. PATENT DOCUMENTS

| | | | |
|---|---|---|---|
| 6,025,287 A | 2/2000 | Hermann | |
| 6,083,185 A | 7/2000 | Lamont | |
| 6,211,426 B1 | 4/2001 | Abrams | |
| 6,513,264 B2 | 2/2003 | Sinaie | |
| 7,141,032 B2 | 11/2006 | Flam et al. | |
| 2006/0189909 A1 | 8/2006 | Hurley et al. | |
| 2007/0282562 A1* | 12/2007 | Schwartz | A43B 17/00 702/139 |
| 2008/0271340 A1 | 11/2008 | Grisoni et al. | |
| 2009/0215952 A1* | 8/2009 | Guy | A43B 13/04 524/492 |
| 2010/0143651 A1* | 6/2010 | Silvis | B32B 27/08 428/141 |
| 2011/0035960 A1* | 2/2011 | Werremeyer | A43B 7/142 36/28 |
| 2011/0232129 A1* | 9/2011 | Roberts | A43B 7/1425 36/88 |
| 2015/0075030 A1* | 3/2015 | Walborn | A43B 1/0009 36/44 |
| 2015/0128335 A1* | 5/2015 | Dehni | A41D 13/0512 2/459 |
| 2017/0011657 A1 | 1/2017 | Chanda et al. | |
| 2017/0280789 A1* | 10/2017 | Wilson | A61F 13/08 |
| 2017/0291331 A1* | 10/2017 | Koo | B29C 41/30 |

OTHER PUBLICATIONS

R. Salcido et al., "Pressure ulcers and wound care," *The Medscape Journal of Medicine*, 2009. Available at: http://emedicine.medscape.com/article/319284-overview. Accessed Sep. 11, 2013.

B. Easterlin et al., "A novel technique of vacuum-assisted wound closure that functions as a delayed primary closure," *Wounds*, vol. 19, p. 331, 2007.

A. Chanda et al., "Biofidelic Human Brain Tissue Surrogates," *Mechanics of Advanced Materials and Structures* (MAMS), 2016.

A. N. Annaidh et al., "Characterization of the anisotropic mechanical properties of excised human skin," *Journal of the Mechanical Behavior of Biomedical Materials*, vol. 5, pp. 139-148, 2012.

E. Eils et al., "Characteristic plantar pressure distribution patterns during soccer-specific movements," *The American Journal of Sports Medicine*, vol. 32, pp. 140-145, 2004.

A. Chanda et al., "Effect of blasts on subject-specific computational models of skin and bone sections at various locations on the human body," 2015.

* cited by examiner

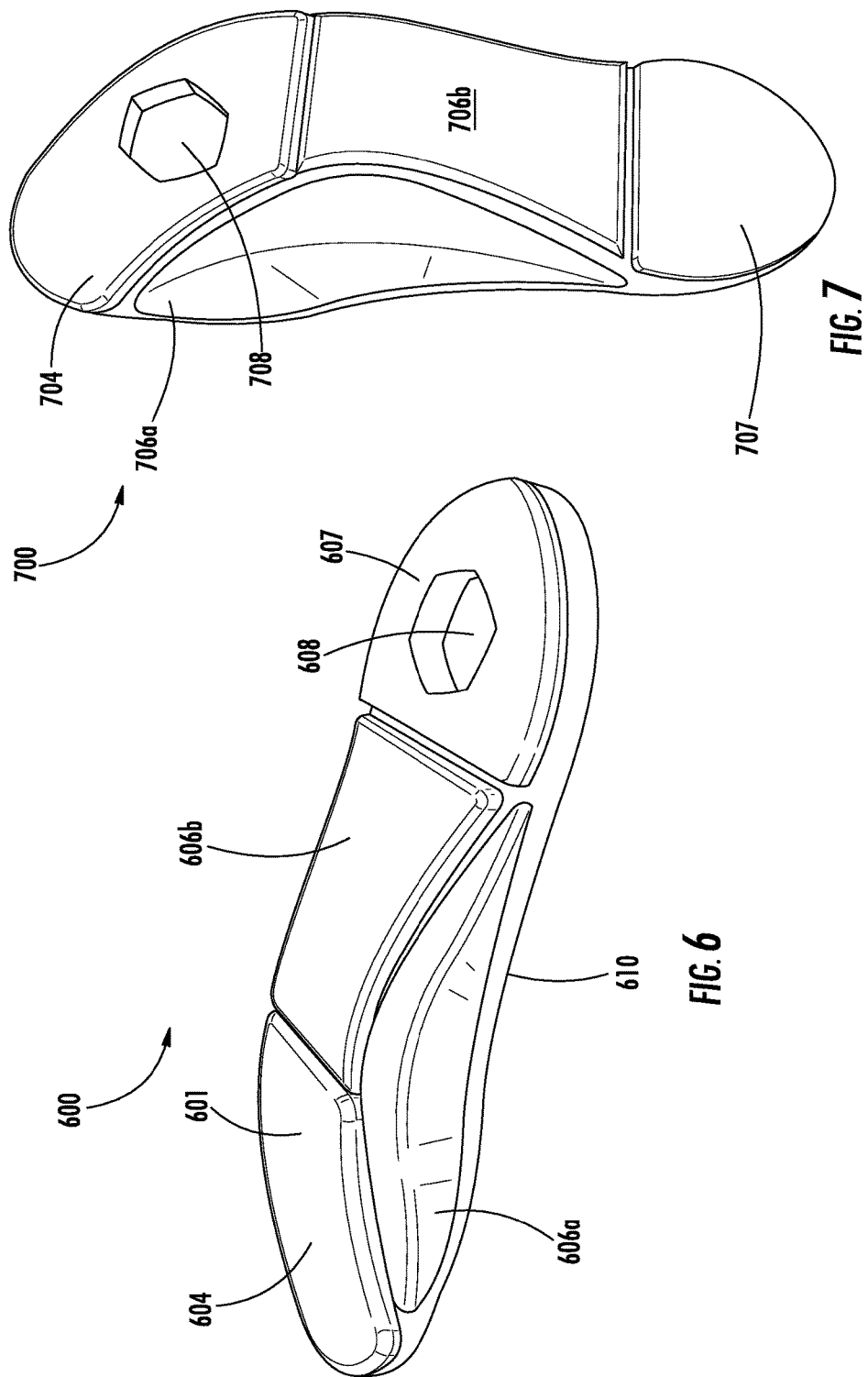

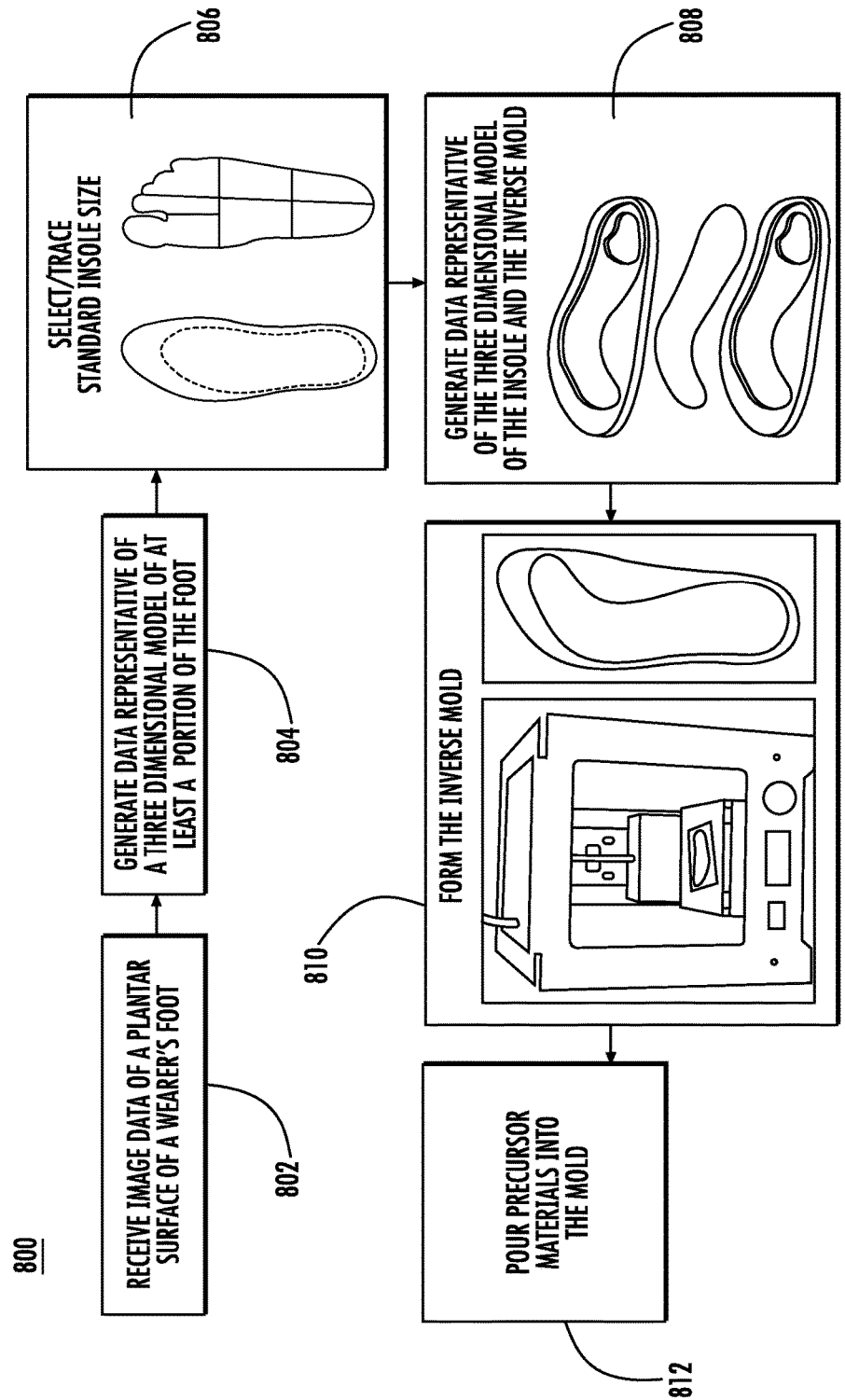

CUSTOMIZED INSOLES FOR DIABETIC AND PRESSURE ULCERS

CROSS REFERENCE TO RELATED APPLICATIONS

This application claims priority to U.S. Provisional Patent Application No. 62/360,773, entitled "Customized Insoles for Diabetic and Pressure Ulcers," filed Jul. 11, 2016, the content of which is herein incorporated by reference in its entirety.

BACKGROUND

Over 20 percent of the 400 million diabetic patients all around the world have foot ulcers. Foot ulcers can be caused by loss of circulation and sensitivity of the skin on the foot, consequently leading to its embrittlement and vulnerability to cracking. The most common sites for occurrence of a foot ulcer are the high pressure points namely the toes, metatarsals, arch, and the heel. An offloading boot can be used to walk with a toe ulcer, as it redistributes the foot pressure onto the heel with minimal pressure transmitted to the toe. However, often, excessive heel pressure may cause the development of heel ulcers. The only technology available in the market for heel ulcers is a total contact cast (TCC) or a plaster. TCC's are also used for toe ulcers that get worse (in terms of size and healing) with time. In some cases, ulcers are also observed at the arch of the foot, which can also be covered using a TCC. The most common issues with both the offloading boot and the TCC are reduced mobility, the requirement of wound dressing on a daily or weekly basis, and slow wound healing (due to all time encapsulation of the ulcers and no contact with the atmosphere). If not taken care of, the ulcers can require a foot amputation. The current treatment for foot ulcers is the V.A.C (Vacuum Assisted Closure), in which the patient must either sit in a wheelchair or is confined to bed rest. Currently, patients with foot ulcers have no way to continue leading their normal life, go to work, socialize or perform their regular activities. Also, besides physical trauma, there is a huge amount of mental trauma which these patients often go through.

Current products focus on prevention of diabetic ulcers rather than their cure and management. The technologies invented for the treatment of diabetic ulcers were mostly in the form of bandages and protective ulcer enclosures which hinders patient mobility. Ulcer isolation has been explored in combination with a TCC, however, the drawbacks associated with TCC persist.

There remains a need for improved footwear for diabetic patients. There remains a need for readily available insoles capable of preventing and/or reducing the incident of foot ulcers. There remains a need for low cost, practical treatments of foot ulcers.

BRIEF SUMMARY

In accordance with the purposes of the disclosed methods, as embodied and broadly described herein, the disclosed subject matter relates to compositions and methods of making and using the compositions. More specifically, according to the aspects illustrated herein, there are provided customized insoles and methods of making and using the customized insoles disclosed herein.

According to various implementations, an insole has a support layer, and the support layer comprises one or more support regions. Each support region comprises a support material simulating biomechanical properties of human skin. The support material comprises an elastomeric network having an elasticity modulus low stretch ratio from 2-8 MPa and an elasticity modulus high stretch ratio from 6-90 MPa, wherein the elasticity modulus high stretch ratio is greater than the elasticity modulus low stretch ratio. In some implementations, the elastomeric network comprises a crosslinked siloxane network comprising a first siloxane having a Shore Hardness of from 00-0 to 00-15 and a second siloxane having a Shore Hardness of from 10 A to 60 A. In some implementations, the first siloxane is present in an amount that is no more than 20% by weight relative to the total weight of the elastomeric network, and the second siloxane is present in an amount that is at least 80% by weight relative to the total weight of the elastomeric network.

According to various implementations, an insole has a support layer, and the support layer comprises a heel support region. The heel support region comprises a heel support material simulating biomechanical properties of human skin. The heel support material comprises a heel elastomeric network having an elasticity modulus low stretch ratio from 2-8 MPa and an elasticity modulus high stretch ratio from 6-90 MPa, wherein the elasticity modulus high stretch ratio is greater than the elasticity modulus low stretch ratio. In some implementations, the heel elastomeric network comprises a crosslinked siloxane network comprising a first heel siloxane having a Shore Hardness of from 00-0 to 00-15 and a second heel siloxane having a Shore Hardness of from 10 A to 60 A. In some implementations, the first heel siloxane is present in an amount that is no more than 20% by weight relative to the total weight of the heel elastomeric network, and the second heel siloxane is present in an amount that is at least 80% by weight relative to the total weight of the heel elastomeric network.

In some implementations, the support layer further comprises a midfoot support region. The midfoot support region comprises a midfoot support material simulating biomechanical properties of human skin. The midfoot support material comprises a midfoot elastomeric network having an elasticity modulus low stretch ratio from 2-8 MPa and an elasticity modulus high stretch ratio from 6-90 MPa, wherein the elasticity modulus high stretch ratio of the midfoot elastomeric network is greater than the elasticity modulus low stretch ratio of the midfoot elastomeric network. In certain implementations, the midfoot elastomeric network comprises a crosslinked siloxane network comprising a first midfoot siloxane having a Shore Hardness of from 00-0 to 00-15 and a second midfoot siloxane having a Shore Hardness of from 10 A to 60 A. In certain implementations, the first midfoot siloxane is present in an amount that is no more than 20% by weight relative to the total weight of the midfoot elastomeric network, and the second midfoot siloxane is present in an amount from that is at least 80% by weight relative to the total weight of the midfoot elastomeric network.

In some implementations, the support layer further comprises a forefoot support region. The forefoot support region comprises a forefoot support material simulating biomechanical properties of human skin. The forefoot support material comprises a forefoot elastomeric network having an elasticity modulus low stretch ratio from 2-8 MPa, and an elasticity modulus high stretch ratio from 6-90 MPa wherein the elasticity modulus high stretch ratio of the forefoot elastomeric network is greater than the elasticity modulus low stretch ratio of the forefoot elastomeric network. In certain implementations, the forefoot elastomeric network comprises a crosslinked siloxane network comprising a first forefoot siloxane having a Shore Hardness of from 00-0 to 00-15 and a second forefoot siloxane having a Shore Hardness of from 10 A to 60 A. In certain implementations, the first forefoot siloxane is present in an amount from that is no more than 20% by weight relative to the total weight of the forefoot elastomeric network, and the second forefoot siloxane is present in an amount from that is at least 80% by weight relative to the total weight of the forefoot elastomeric network.

In some implementations, a first surface of the support layer is configured for facing a plantar surface of a user's foot, and the first surface defines a recessed portion. In certain implementations, the recessed portion is arranged to receive one or more lateral portions of the user's foot. In certain implementations, the recessed portion extends between the lateral midfoot support region and the lateral heel support region of the support layer. For example, in one implementation, the recessed portion further extends into at least a portion of the forefoot support region. In further or alternative implementations, the first surface of the support layer comprises a recessed portion arranged to receive one or more medial portions of the user's foot. In certain implementations, a sweat absorbent material disposed at least within the recessed portion. And, in a further or alternative implementation, an anti-microbial material disposed at least within the recessed portion.

In some implementations, a second surface of the support layer is opposite and spaced apart from the first surface of the support layer, and the insole further comprises a base layer coupled to the second surface of the support layer.

In some implementations, at least one region of the support layer defines an isolation segment that defines a recess, and the recess extends through a first surface of the support layer toward a second surface of the support layer that is opposite and spaced apart from the first surface. The isolation segment has a perimeter that corresponds to a perimeter of a skin injury on a plantar surface of a user's foot, wherein the first surface faces the plantar surface of the user's foot in use.

In some implementations, at least one support region of the support layer defines an isolation segment, and the isolation segment comprises an isolation segment siloxane having a Shore hardness that is less than the Shore hardness of the siloxane in the at least one support region defining the isolation segment.

In various implementations, a method of manufacturing an insole comprises receiving data representative of a three dimensional model of at least a portion of a plantar surface of a user's foot; forming an inverse mold of the three dimensional model, the inverse mold having at least a heel region; and pouring a heel precursor material into the heel region of the inverse mold, the heel precursor material comprising a first heel siloxane having a Shore Hardness of from 00-0 to 00-15 and a second heel siloxane having a Shore Hardness of from 10 A to 60 A, wherein the first and second heel siloxanes are different.

In some implementations, the method further includes receiving image data associated with the portion of the plantar surface of the user's foot; identifying dimensions and a contour of the portion of the plantar surface using the received image data; and generating the data representative of the three dimensional model based on the identified dimensions and contour of the portion of the plantar surface.

In some implementations, the heel region comprises a lateral heel region and a medial heel region, and the lateral heel region and the medial heel region are divided by a heel region wall. The heel precursor material is a first heel precursor material and is poured into the lateral heel region, and the method further comprises pouring a second heel precursor material into the medial heel region of the inverse mold. The second heel precursor material has a first medial heel siloxane having a Shore hardness of from 00-0 to 00-15 and a second medial heel siloxane having a Shore hardness of from 10 A to 60 A, wherein the first and second medial heel siloxanes are different.

In some implementations, the inverse mold comprises a midfoot region and a wall between the midfoot region and the heel region, and the method further comprises pouring a midfoot precursor material into the midfoot region of the inverse mold. The midfoot precursor material comprises a first midfoot siloxane having a Shore Hardness of from 00-0 to 00-15 and a second midfoot siloxane having a Shore Hardness of from 10 A to 60 A, wherein the first and second midfoot siloxanes are different. In certain implementations, the midfoot region comprises a lateral midfoot region and a medial midfoot region. The lateral midfoot region and the medial midfoot region are divided by a midfoot region wall, and the midfoot precursor material is a first midfoot precursor material and is poured into the lateral midfoot region. The method further comprises pouring a second midfoot precursor material into the medial midfoot region of the inverse mold. The second midfoot precursor material has a first medial midfoot siloxane having a Shore hardness of from 00-0 to 00-15 and a second medial midfoot siloxane having a Shore hardness of from 10 A to 60 A, wherein the first and second medial midfoot siloxanes are different.

In certain implementations, the wall is a first wall, and the inverse mold further comprises a forefoot region and a second wall between the forefoot region and the midfoot region. The method further comprises pouring a forefoot precursor material into the forefoot region of the inverse mold. The forefoot precursor material has a first forefoot siloxane having a Shore hardness of from 00-0 to 00-15 and a second forefoot siloxane having a Shore hardness of from 10 A to 60 A, wherein the first and second forefoot siloxanes are different.

In some implementations, the forefoot region comprises a lateral forefoot region and a medial forefoot region. The lateral forefoot region and the medial forefoot region are divided by a forefoot region wall, and the forefoot precursor material is a first forefoot precursor material and is poured into the lateral forefoot region. The method further comprises pouring a second forefoot precursor material into the medial forefoot region of the inverse mold. The second forefoot precursor material has a first medial forefoot siloxane having a Shore hardness of from 00-0 to 00-15 and a second medial forefoot siloxane having a Shore hardness of from 10 A to 60 A, wherein the first and second medial forefoot siloxanes are different.

In some implementations, the medial forefoot region comprises a first metatarsal forefoot region and a second metatarsal forefoot region. The first metatarsal forefoot region and the second metatarsal forefoot region are divided by a metatarsal forefoot region wall, and the second forefoot precursor material is poured into the first metatarsal forefoot region. The method further comprises pouring a third forefoot precursor material into the second metatarsal forefoot region of the inverse mold. The third forefoot precursor material has a third medial forefoot siloxane having a Shore hardness of from 00-0 to 00-15 and a fourth medial forefoot siloxane having a Shore hardness of from 10 A to 60 A, wherein the third and fourth medial forefoot siloxanes are different.

In some implementations, identifying the contour of the portion of the plantar surface of the user's foot comprises identifying a skin injury on the plantar surface adjacent a heel, midfoot, or forefoot portion of the user's foot, and forming the inverse mold comprises forming a protrusion corresponding to the location and shape of the skin injury. The protrusion causes the portion of the support layer for being disposed adjacent the skin injury to define an isolation segment defining a recess that extends through a first surface of the support layer toward a second surface of the support layer.

In alternative or further implementations, identifying the contour of the portion of the plantar surface of the user's foot comprises identifying a skin injury on the plantar surface adjacent a heel, midfoot, or forefoot portion of the human foot, and forming the inverse mold comprises forming an isolation segment wall corresponding to the location and shape of the skin injury. The method further comprises pouring an isolation segment precursor material having an isolation segment siloxane having a Shore hardness that is less than the Shore hardness of the siloxane poured into one or more regions adjacent the isolation segment wall.

In some implementations, forming the inverse mold comprises additive manufacturing.

Additional advantages are set forth in part in the description that follows or may be learned by practice of the aspects described below. The advantages described below are realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying figures, which are incorporated in and constitute a part of this specification, illustrate several aspects described below.

FIG. 6 illustrates a custom insole, according to another implementation.

FIG. 7 illustrates a custom insole, according to another implementation.

FIG. 8 illustrates steps in a method of producing a custom insole according to various implementations.

DETAILED DESCRIPTION

Figure 1:
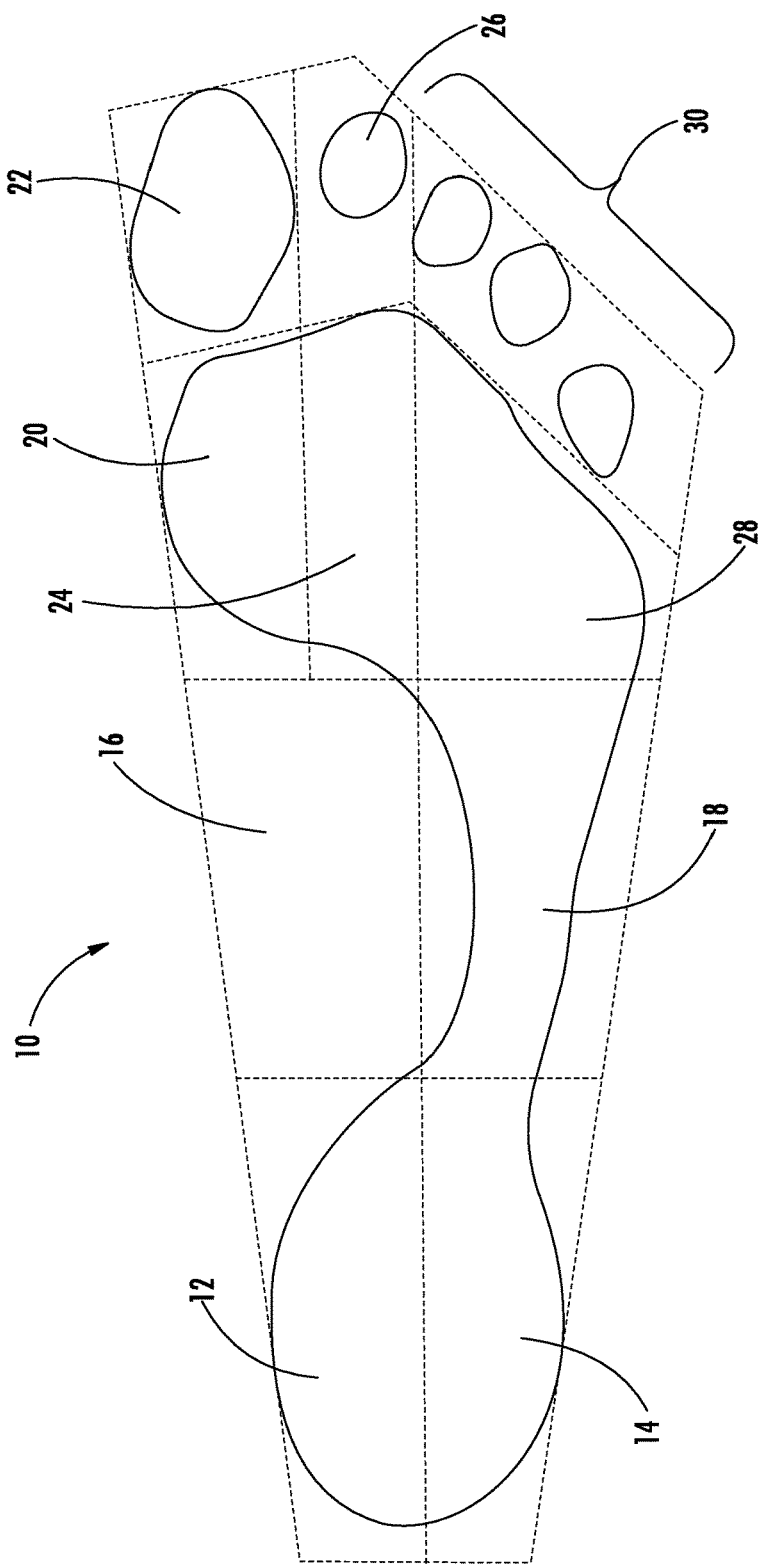
FIG. 1 includes a schematic diagram of regions of a wearer's foot, according to one implementation.

The methods and compositions described herein may be understood more readily by reference to the following detailed description of specific aspects of the disclosed subject matter and the Examples included therein.

Before the present methods and compositions are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

It is understood that throughout this specification the identifiers "first," "second," and other ordinal numbers are used solely to aid the reader in distinguishing the various components, features, or steps of the disclosed subject matter. The identifiers "first," "second," and other ordinal numbers are not intended to imply any particular order, amount, preference, or importance to the components or steps modified by these terms.

By substantially the same is meant the values are within 5% of one another, e.g., within 3%, 2%, or 1% of one another.

As used herein, the term "ulcer" refers to an open sore or wound occurring on an external surface of the body, for instance, the sole of the foot. Foot ulcers can result from peripheral neuropathy, for instance caused by diabetes. Peripheral neuropathy damages nerves, causing individuals to lose sensation. Individuals with peripheral neuropathy in their feet can sustain a minor injury, which, because it is not detected, can be exacerbated into an ulcer. Foot ulcers can also be caused by peripheral artery disease, which can lead to reduced circulation in the feet. Reduced circulation can both increase likelihood of injury and also decrease the ability of the skin to heal.

As used herein, the term "silicone rubber" refers to three-dimensional networks of cross-linked siloxane polymers. Unless specified otherwise, silicone rubbers include materials that are composed solely of crosslinked siloxane polymers and materials that include other chemical compounds incorporated into the network. Such other chemical compounds can be covalently incorporated into the network or can be incorporated into the network through non-covalent interactions (e.g., hydrogen bonds, electrostatic bonds, Van der Waal bonds and the like).

As used herein, the term "non-linear hyperelastic" describes a material in which some specified influence (such as stress) produces a response (such as strain or stretch) which is not proportional to the influence and which can be characterized using constitutive curve fit equations known as the hyperelastic equations.

As used herein, the term "elasticity modulus (E) low stretch ratio" refers to the initial elasticity modulus or slope of the stress-stretch plot of a non-linear material approximated at low stretch values. The elasticity modulus (E) low stretch ratio is measured by drawing a line starting at the origin and tangent to the stress-stretch plot and numerically estimate its slope.

As used herein, the term "elasticity modulus (E) high stretch ratio" refers to the final elasticity modulus or slope of the stress-stretch plot of a non-linear material before rupture. The elasticity modulus (E) high stretch ratio is measured by drawing a line starting at the point of rupture and tangent to the stress-stretch plot and numerically estimating its slope.

A material that exhibits non-linear hyperelasticity is characterized by differing elastic moduli in the high-stretch and low-stretch region.

As used herein, the term "ultimate tensile strength" refers to the value of stress applied to a material which just causes its rupture.

As used herein, the term "one-part siloxane" refers to a liquid siloxane composition which undergoes crosslinking in the absence of any added chemical reagent. Exemplary one-part siloxanes include those cured by heat, light, moisture, and combinations thereof. Some one-part siloxanes can undergo crosslinking when exposed to ambient conditions (~23° C., standard humidity), whereas others require additional energy inputs (such as light or elevated heat) in order to crosslink.

As used herein, the term "two-part siloxane (Part A)," or simply "siloxane (Part A)," refers to a liquid siloxane composition that contains a latent reactive silicone functional group that requires activation by the exposure to an additional chemical reagent.

As used herein, the term "two-part siloxane (Part B)," or simply "siloxane (Part B)," refers to a liquid siloxane composition that contains a chemical reagent that activates a silicone functional group to crosslinking.

Crosslinked siloxane networks can be characterized according to the Shore (Durometer) hardness scale, as defined by the American Society for Testing and Materials (ASTM) D2240 testing standard. Shore (Durometer) hardness can be measured along several different scales, including "00", "A," and "D". Skin simulants can have, but are not limited to, networks having a Shore (Durometer) hardness from 00-10 to 00-60.

As used herein, the term "siloxane 00-10" refers to a liquid siloxane composition, which, when cured with another siloxane 00-10, produces a silicone network having a Shore (Durometer) hardness of 00-10. One of ordinary skill will appreciate that when a siloxane (Part A) 30 A is combined with an equal amount of siloxane (Part B) 30 A, the resulting network will have a Shore (Durometer) hardness of 30 A. However, when two siloxanes of differing Shore (Durometer) hardness levels are combined, the resulting network has a Shore hardness different than either of the precursor siloxane components.

Customized Insoles

Various implementations include customized insoles that include a support layer having a first surface that faces a plantar surface of a wearer's foot in use. The size and contour of the first surface, the shape and number of support regions of the support layer, and the support materials selected for each support region are customized based on the size and contour of the plantar surface of the wearer's foot, the expected loads and/or stresses on the foot (e.g., based on the wearer's weight, foot structure, and daily activities), the level of support needed (e.g., firmness or cushioning), and/or the medical condition of the wearer (e.g., diabetic). For example, the first surface of the support layer may define one or more recessed regions that correspond with the contour of the plantar surface of the wearer's foot and/or at least one isolation segment that corresponds with the perimeter of a skin injury on the planter surface of the wearer's foot. Recessed regions may also be provided to adjust the plane in which one or more portions of the foot lie relative to the other portions of the foot.

The support layer also has a second surface that is spaced apart and opposite the first surface. In use, the second surface faces the insole of a shoe in which the insole is disposed. The insole may further include a base layer of material that is coupled to the second surface of the support material, or the insole may not include a separate base layer of material adjacent the second surface of the support layer.

The support layer includes one or more support regions that correspond to one or more portions of the plantar surface of the wearer's foot. Each of the one or more support regions of the support layer are formed from one or more support materials. The composition of the support material in each support region is based on the expected loads/stresses on the wearer's foot and/or medical condition(s) of the wearer. In addition, the support materials are skin simulants, meaning that the materials have biomechanical properties similar to those of natural human skin.

Figure 4:
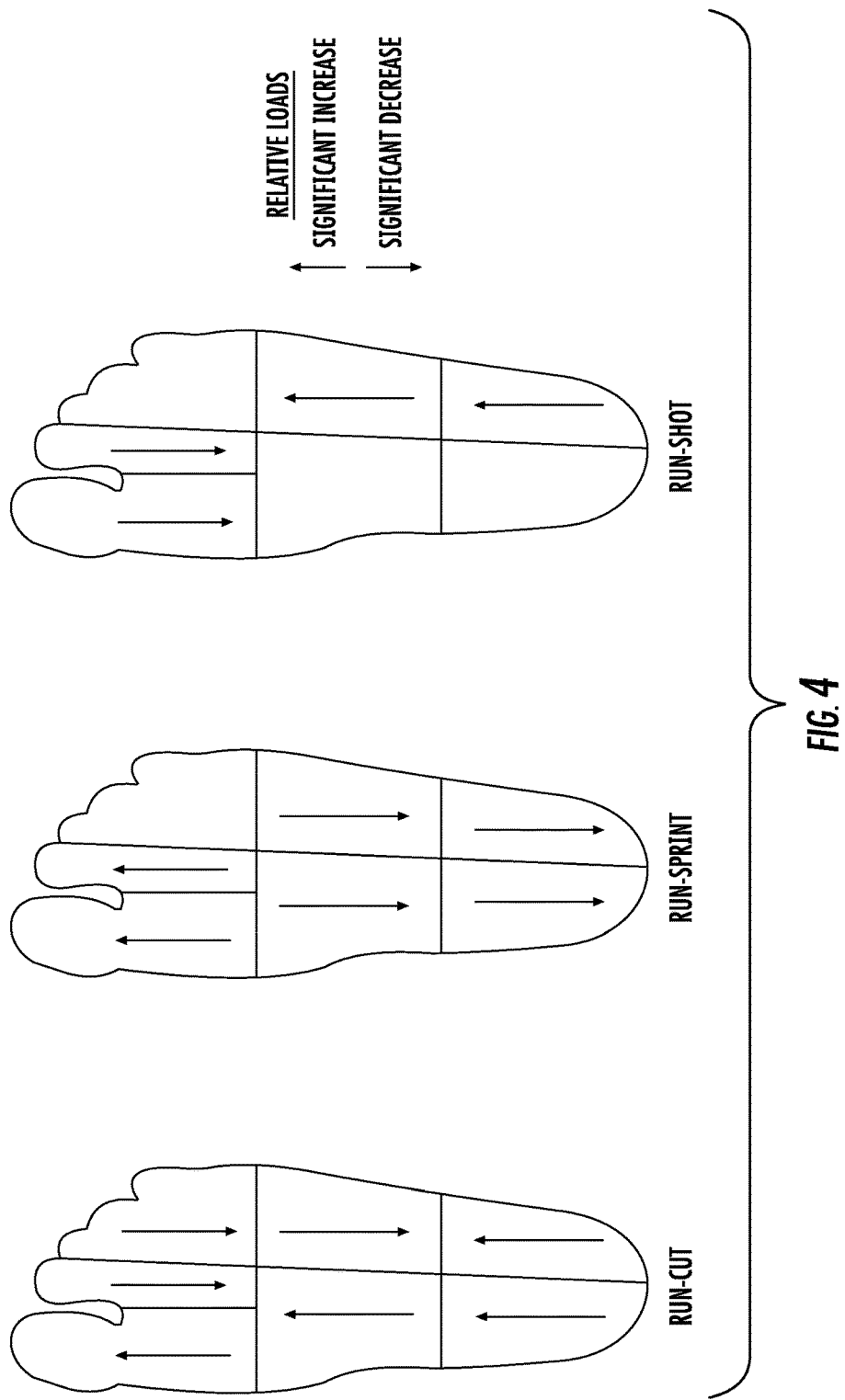
FIG. 4 illustrates various load distributions experienced by a foot during different activities, according to various implementations.

FIG. 4, which was provided in Eils, Eric, et al. "Characteristic plantar pressure distribution patterns during soccer-specific movements," The American Journal of Sports Medicine 32.1 (2004): 140-145, illustrates relative loads on various regions of the foot during a run-cut activity, a run-sprint activity, and a run-shot activity. Regional loads also change in different diabetic conditions, which need to be relieved appropriately to avoid ulcerations. Accordingly, certain portions of the foot may need to contact a firmer material and other regions may need to contact a softer material. The portions of the foot shown in FIG. 4 are illustrated with respect to the corresponding portion of the plantar surface of the wearer's foot in FIG. 1. As shown in FIGS. 1 and 4, the plantar surface 10 of the foot can be divided into a medial heel portion 12, a lateral heel portion 14, a medial midfoot portion 16, a lateral midfoot portion 18, a first metatarsal portion 20, a hallux portion 22, a second metatarsal portion 24, a second toe portion 26, a lateral metatarsals portion 28, and a lateral toes portion 30. However, the plantar surface of the human foot may be divided into more or less portions than those shown in FIGS. 1 and 4, depending on the level of customization for the insole, expected loads and/or stresses for the wearer's foot, and/or the medical condition of the wearer, for example.

Thus, in some implementations, the insole includes two or more support regions, such as, for example, a heel support region, a midfoot support region, and a forefoot support region. And, in certain implementations, one or more support regions may include two or more sub-regions.

Figure 5:
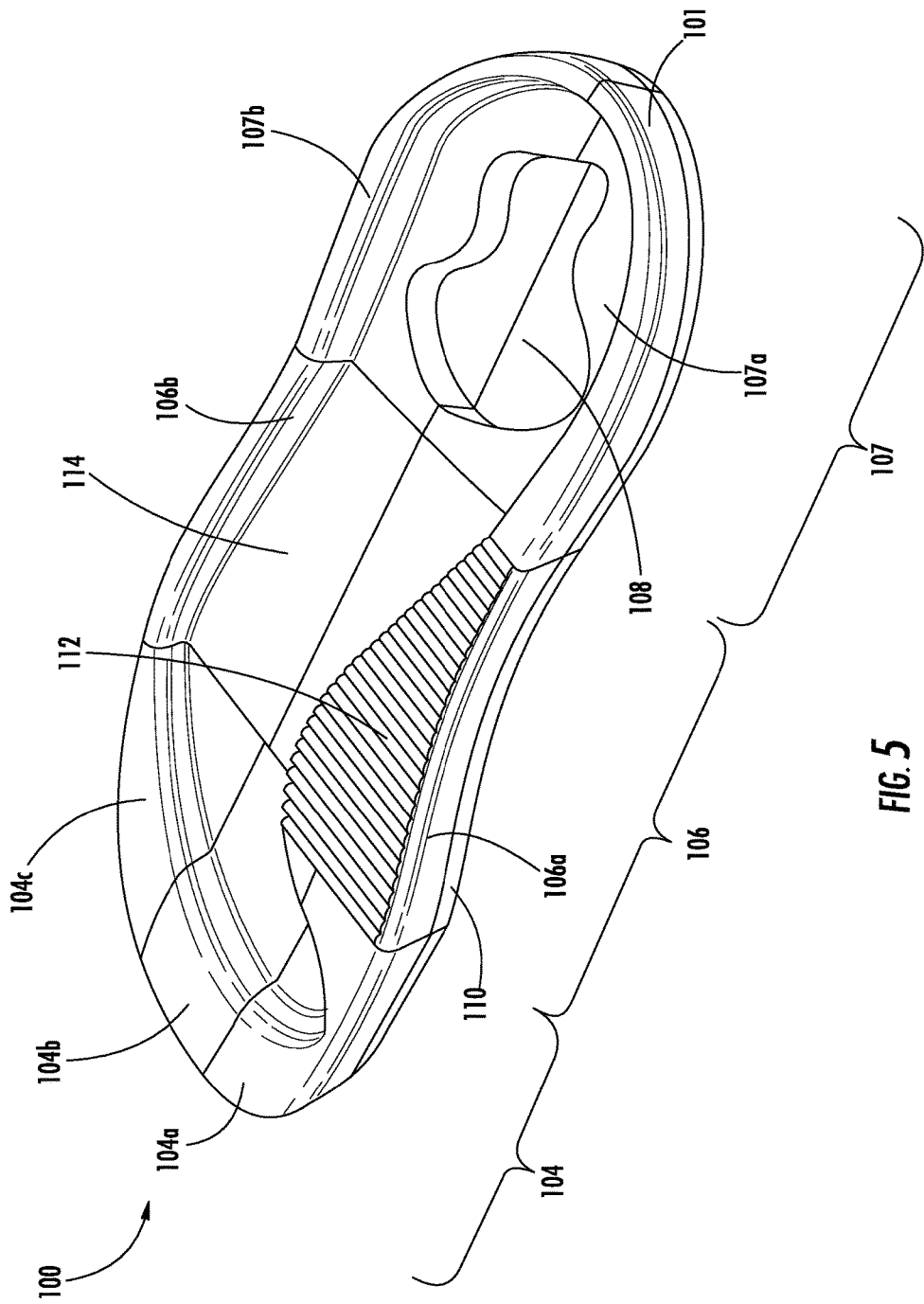
FIG. 5 illustrates a custom insole, according to one implementation.

FIG. 5 illustrates an exemplary implementation of a customized insole 100 having two or more support regions. The insole 100 includes a support layer 101 and a base layer 110. The support layer 101 includes a first surface 112 and a second surface (not shown in FIG. 5) that is opposite and spaced apart from the first surface 112. The first surface 112 faces the plantar surface of the wearer's foot in use. In addition, the support layer 101 includes a heel support region 107 that includes a medial heel support region 107a and a lateral heel support region 107b, a midfoot support region 106 that includes a medial midfoot support region 106a and a lateral midfoot support region 106b, and a forefoot support region 104 that includes a first metatarsal support region 104a, a second metatarsal support region 104b, and a lateral metatarsal support region 104c. The heel support region 107 is adjacent the calcaneus bone when in use. The midfoot support region 106 is adjacent the cuneiform bones, cuboid bone, and navicular bone when in use. The midfoot support region 106 may also extend below a proximal portion of the metatarsal bones of the wearer when in use, according to some implementations. The first metatarsal support region 104a is adjacent the hallux, first phalange, and at least a distal portion of the first metatarsal bone when in use. The second metatarsal support region 104b is adjacent the second phalanges and at least a distal portion of the second metatarsal bone when in use. And, the lateral metatarsal support region 104c is adjacent the third through fifth phalanges and at least a distal portion of the third through fifth metatarsal bones when in use.

In other implementations, the forefoot support region can be divided into multiple support regions (e.g., two or more phalange and/or metatarsal support regions, such as five metatarsal support regions). And, in other implementations, the forefoot support region can be divided into a hallux region, a second phalanges region, a lateral phalanges region, and/or one or more metatarsal support regions.

In certain implementations, the support layer 101 can define one or more isolation segments, such as isolation segment 108 shown in FIG. 5. The isolation segment 108 is a hole or recess cut out of or formed into the support layer 101 that aligns with a location of a skin injury (e.g., an ulcer, blister, cut, or sore) on the planter surface of the wearer's foot when in use. The isolation segment 108 can be customized to the shape of the injury area, in some implementations. For example, in some implementations, a perimeter of the isolation segment 108 has the same or similar shape as the perimeter of the skin injury and is offset in a radially outward direction from the perimeter of the skin injury when in use. In other words, the perimeter of the isolation segment 108 is larger than the perimeter of the skin injury to avoid having the support layer 101 contact the skin injury. By providing the isolation segment 108 adjacent the skin injury, pressure is reduced on the injured tissue, speeding recovery and minimizing further damage. The support layer 101 can have multiple isolation segments, depending on the number of ulcers affecting the patient. In some implementations, the isolation segment 108 is a recess defined in the first surface 112 that extends toward the second surface but does not extend fully through the support layer 101. In other implementations, the recess extends fully through the first 112 and second surfaces of the support layer 101. And, in other implementations, the recess extends fully through the support layer 101 and base layer 110.

Figure 11:
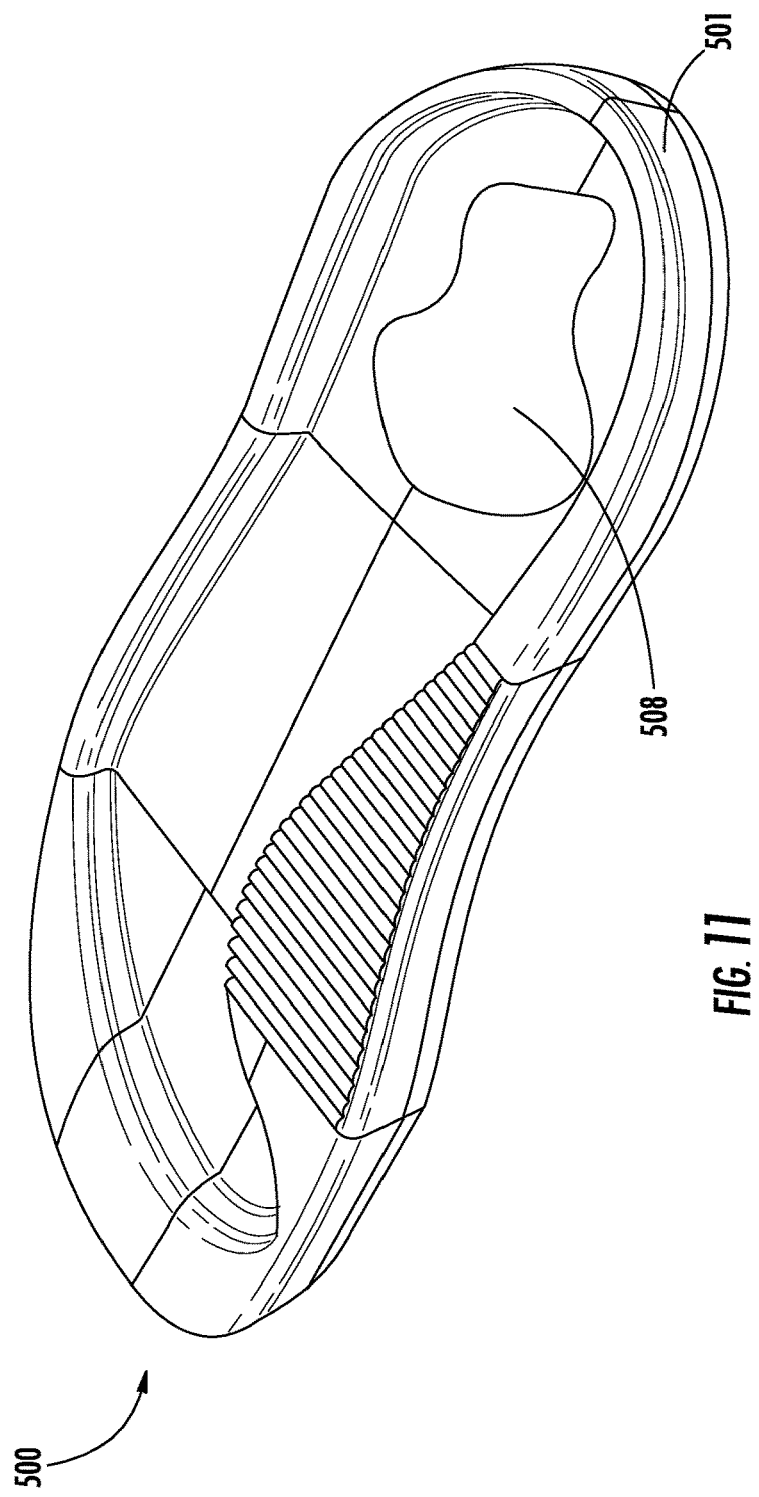
FIG. 11 illustrates a custom insole formed using the mold in FIG. 10, according to one implementation.

In other implementations, such as shown in FIG. 11, the isolation segment 508 is a region of the support layer 501 of insole 500 and comprises a material that is softer than the material surrounding it. For instance, the isolation segment 508 can include a siloxane having a Shore hardness that is less than the Shore hardness of the siloxane in the adjacent support region(s) defining the isolation segment 508. In some embodiments, the isolation segment 508 can include a siloxane having a Shore hardness of from 00-0 to 00-20, from 00-0 to 00-15, from 00-0 to 00-10, or from 00-0 to 00-05.

In some implementations, such as shown on surface 112 in FIG. 5, one or more portions of the first surface can be textured, such as having ridges, protrusions, recesses, or other suitable texture pattern. Texture may be provided to reduce contact with the skin, provide additional grip, and/or to provide ventilation between the skin and the first surface 112 of the support layer 101.

The first surface 112 of the support layer 101 further defines a recessed portion 114 that extends between the heel support region 107, the lateral midfoot support region 106, and the lateral forefoot region 104. The difference in height between the recessed portion 114 and a non-recessed portion of the first surface 112 may be selected based on the contour of the plantar surface of the wearer's foot and/or to raise or lower at least a portion of the medial side of the wearer's foot relative to at least a portion of the lateral side of the wearer's foot.

Figure 2:
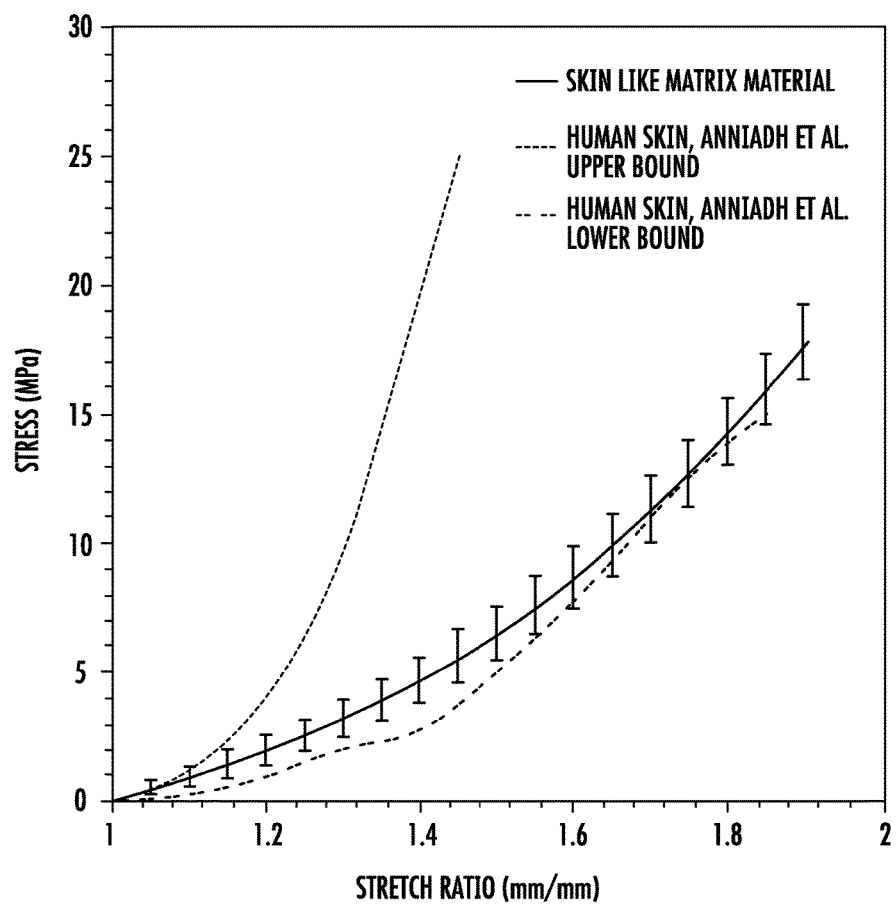
FIG. 2 is a stretch-stress plot for skin-like matrix compared with natural human skin. The stretch ratio is plotted on the x-axis and the stress (MPa) is plotted on the y-axis.

As noted above, the one or more support materials used for the support layer of the insole have biomechanical properties similar to human skin. Skin is a viscoelastic material and exhibits non-linear stress-strain behavior. In particular, the support materials disclosed herein can exhibit non-linear hyper-elasticity, which is more consistent with human skin than other support materials. Biomechanical properties of human skin have been reported by Anniadh et al., in "Characterization of the anisotropic mechanical properties of excised human skin," JOURNAL OF THE MECHANICAL BEHAVIOR OF BIOMEDICAL MATERIALS (2012) 5:139-148, which is incorporated by reference herein in its entirety for its teaching of the mechanical properties of skin and methods of measuring those properties. Anniadh describes the non-linear hyperelastic properties of human skin. In various implementations, the materials disclosed herein for forming the support material of the insoles disclosed herein exhibit non-linear hyperelastic properties falling with the ranges provided by Anniadh for human skin. FIG. 2 illustrates a stretch-stress plot for an exemplary support material compared with natural human skin. The stretch ratio is plotted on the x-axis and the stress (MPa) is plotted on the y-axis.

For example, in some implementations, one or more of the support regions disclosed herein can include support materials comprising elastomeric networks, such as cross-linked siloxane networks. Suitable siloxane polymers for incorporation into the networks include those giving rise to silicone rubbers having a Shore (Durometer) hardness from 00-0 to 60 A, including 00-0, 00-10, 00-20, 00-30, 00-40, 00-50, 00-60, 10 A, 20 A, 30 A, 40 A, 50 A and 60 A as well as intermediate shore hardness, e.g., 00-125, 00-15, 00-175, 15 A, 25 A, 35 A and the like. However, other siloxanes, for instance those which, when cured alone, result in more rigid elastomers, can also be incorporated into the support regions.

In certain implementations, the support materials comprise silicone rubber. Silicone rubber is an elastomeric network of crosslinked siloxane polymers. Some silicone rubbers are characterized as "one-part," whereas others are referred to as "two-part." One and two-part silicone rubbers are distinguished based on how they are cured. One part silicone rubbers are obtained by curing a single liquid siloxane precursor. Crosslinking such one-part systems can occur in the presence of air, light, and/or heat. Two-part silicone rubbers are prepared by combining two separate siloxane liquids. Each part contains a reactive component which, when combined, initiates the crosslinking reaction. Two-part silicone rubbers include addition-cured rubbers such as platinum cure rubbers, condensation-cured rubbers such as tin-cured rubbers, and peroxide-cured rubbers. The individual components of a two-part silicone rubber are often designated "Part A" and "Part B."

In certain implementations, one or more of the support materials of the support layer are made from a single one-part or two-part siloxane. Such support materials are designated herein as "unitary siloxanes." One or more support regions of the support layer can also include two different one-part or two-part siloxanes. Such simulants are designated herein as "binary siloxanes." Higher order systems, such as ternary or quaternary refer to systems made from three, or four, different siloxanes (one-part or two-part), respectively. Generally, multipart siloxane systems include at least one siloxane having a Shore hardness from 00-0 to 00-30 and at least one siloxane having a Shore hardness from 10 A to 60 A.

The subsections below describe exemplary support materials that may be included in each region of the support layer of the insole.

Heel Support Material

In some implementations, the heel support region, such as heel support region 107, comprises a heel support material comprising a heel elastomeric network. The heel elastomeric network can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the heel elastomeric network can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 3.5-8, 3-8, 4-8, 4-7.5, 4-7, 4-6.5, 4-6, 4-5.5, 4-5, 4-4.5 or 2.5-8 MPa.

The heel elastomeric network can also have an elasticity modulus (E) high stretch ratio of at least 6, 13, 20, 27, 34, 41, 48, 55, 62, 69, 76, 83, or 90 MPa, where any of the stated values can form an upper or lower endpoint of a range. The heel elastomeric network can also have an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 27-90, 20-90, or 13-90 MPa.

The heel elastomeric network can be characterized by an ultimate tensile strength of at least 1, 2, 3, 4, 5, 6, 7, 8, 9, 10, 15, 20, or 25 MPa, where any of the stated values can form an upper or lower endpoint of a range. The heel elastomeric network can be characterized by an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10-25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the heel elastomeric network is a blend of at least one siloxane having a Shore hardness from 00-0 to 00-15 and a second siloxane having a Shore hardness from 10 A to 60 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain heel elastomeric networks, the first and second siloxanes can be present in a ratio from 1:99 to 20:80 by weight of the total silicone rubber content. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, heel elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

As noted above, the heel support region may include one or more sub-regions. Such sub-regions of the heel support region include, but are not limited to, the lateral heel support region and the medial heel support region. For example, in the implementation shown in FIG. 5 described above, the heel support region 107 includes the medial heel support region 107a and the lateral heel support region 107b. The below description sets forth exemplary heel support materials used in each sub-region of the heel support region.

Medial Heel Support Material

In some implementations, the medial heel support region, such as medial heel support region 107a, includes medial heel support material that includes a medial heel elastomeric network. The medial heel elastomeric network can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the medial heel elastomeric network can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 4-7.5, 4-7, 4-6.5, 4-6, 4-5.5, 4-5, 4-4.5, 3.5-8, 3-8, or 2.5-8 MPa.

The medial heel elastomeric network can have an elasticity modulus (E) high stretch ratio of at least 6, 13, 20, 27, 34, 41, 48, 55, 62, 69, 76, 83, or 90 MPa, where any of the stated values can form an upper or lower endpoint of a range.

The medial heel elastomeric network can have an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 27-90, 20-90, or 13-90 MPa.

The medial heel elastomeric network can have an ultimate tensile strength of at least 1, 2, 3, 4, 5, 6, 7, 8, 9, 10, 15, 20, or 25 MPa, where any of the stated values can form an upper or lower endpoint of a range. The medial heel elastomeric network can have an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10-25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the medial heel elastomeric network is a blend of at least one siloxane having a Shore hardness from 00-0 to 00-15 and a second siloxane having a Shore hardness from 10 A to 60 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain medial heel elastomeric networks, the first and second siloxanes can be present in a ratio from 1:99 to 20:80 by weight of the total silicone rubber content. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, medial heel elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

Lateral Heel Support Material

In some implementations, the lateral heel support region, such as lateral heel support region 107b, includes a lateral heel support material that includes a lateral heel elastomeric network. The lateral heel elastomeric network can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the lateral heel elastomeric network can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 4-7.5, 4-7, 4-6.5, 4-6, 4-5.5, 4-5, 4-4.5, 3.5-8, 3-8, or 2.5-8 MPa.

The lateral heel elastomeric network can have an elasticity modulus (E) high stretch ratio of at least 6, 13, 20, 27, 34, 41, 48, 55, 62, 69, 76, 83, or 90 MPa, where any of the stated values can form an upper or lower endpoint of a range. The lateral heel elastomeric network can have an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 27-90, 20-90, or 13-90 MPa.

The lateral heel elastomeric network can have an ultimate tensile strength of at least 1, 2, 3, 4, 5, 6, 7, 8, 9, 10, 15, 20, or 25 MPa, where any of the stated values can form an upper or lower endpoint of a range. The lateral heel elastomeric network can have an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10-25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the lateral heel elastomeric network is a blend of at least one siloxane having a Shore hardness from 00-0 to 00-15 and a second siloxane having a Shore hardness from 10 A to 60 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain types of lateral heel elastomeric networks, the first and second siloxanes can be present in a ratio from 1:99 to 20:80 by weight of the total silicone rubber. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, lateral heel elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

Midfoot Support Material

In some implementations, the midfoot support region, such as midfoot support region 106, includes a midfoot support material that includes a midfoot elastomeric network. The midfoot elastomeric network can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the midfoot elastomeric network can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 4-7.5, 4-7, 4-6.5, 4-6, 4-5.5, 4-5, 4-4.5, 3.5-8, 3-8, or 2.5-8 MPa.

The midfoot elastomeric network can have an elasticity modulus (E) high stretch ratio of at least 6, 13, 20, 27, 34, 41, 48, 55, 62, 69, 76, 83, or 90 MPa, where any of the stated values can form an upper or lower endpoint of a range. The midfoot elastomeric network can have an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 83-90, 76-90, 27-90, 20-90, or 13-90 MPa.

The midfoot elastomeric network can have an ultimate tensile strength of at least 1, 2, 3, 4, 5, 6, 7, 8, 9, 10, 15, 20, or 25 MPa, where any of the stated values can form an upper or lower endpoint of a range. The midfoot elastomeric network can have an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10- to 25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the midfoot elastomeric network is a blend of at least one siloxane having a Shore hardness from 00-0 to 00-15 and a second siloxane having a Shore hardness from 10 A to 60 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain midfoot elastomeric networks, the first and second siloxanes can be present in a ratio from 1:99 to 20:80 by weight of the total silicone rubber. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, midfoot elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

As noted above, the midfoot support region may include one or more sub-regions. Such sub-regions of the midfoot support region include, but are not limited to, the lateral midfoot support region and the medial midfoot support region. For example, in the implementation shown in FIG. 5 described above, the midfoot support region 106 includes a medial midfoot support region 106a and lateral midfoot support region 106b. The below description sets forth exemplary midfoot support materials used in each sub-region of the midfoot support region.

Medial Midfoot Support Material

In some implementations, the medial midfoot support region (also called the arch support region), such as medial midfoot support region 106a, includes a medial midfoot support material that includes a medial midfoot elastomeric network. The medial midfoot elastomeric network can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the medial midfoot elastomeric network can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 4-7.5, 4-7, 4-6.5, 4-6, 4-5.5, 4-5, 4-4.5, 3.5-8, 3-8, or 2.5-8 MPa.

The medial midfoot elastomeric network can have an elasticity modulus (E) high stretch ratio of at least 6, 13, 20, 27, 34, 41, 48, 55, 62, 69, 76, 83, or 90 MPa, where any of the stated values can form an upper or lower endpoint of a range. The medial midfoot elastomeric network has an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 27-90, 20-90, or 13-90 MPa.

The medial midfoot elastomeric network can have an ultimate tensile strength of at least 1, 2, 3, 4, 5, 6, 7, 8, 9, 10, 15, 20, or 25 MPa, where any of the stated values can form an upper or lower endpoint of a range. The medial midfoot elastomeric network can have an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10-25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the medial midfoot elastomeric network is a blend of at least one siloxane having a Shore hardness from 00-0 to 00-15 and a second siloxane having a Shore hardness from 10 A to 60 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain types of medial midfoot elastomeric networks, the first and second siloxanes can be present in a ratio from 1:99 to 20:80 by weight of the total silicone rubber. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, medial midfoot elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

Lateral Midfoot Support Material

In some implementations, the lateral midfoot support region (also called the soft midfoot support region), such as lateral midfoot support region 106b, includes a lateral midfoot support material that includes a lateral midfoot elastomeric network. The lateral midfoot elastomeric network can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the lateral midfoot elastomeric network can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 4-7.5, 4-7, 4-6.5, 4-6, 4-5.5, 4-5, 4-4.5, 3.5-8, 3-8, or 2.5-8 MPa.

The lateral midfoot elastomeric network can have an elasticity modulus (E) high stretch ratio of at least 6, 13, 20, 27, 34, 41, 48, 55, 62, 69, 76, 83, or 90 MPa, where any of the stated values can form an upper or lower endpoint of a range. The lateral midfoot elastomeric network can have an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 27-90, 20-90, or 13-90 MPa.

The lateral midfoot elastomeric network can have an ultimate tensile strength of at least 1, 2, 3, 4, 5, 6, 7, 8, 9, 10, 15, 20, or 25 MPa, where any of the stated values can form an upper or lower endpoint of a range. The lateral midfoot elastomeric network can have an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10-25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the lateral midfoot elastomeric network is a blend of at least one siloxane having a Shore hardness from 00-0 to 00-15 and a second siloxane having a Shore hardness from 10 A to 60 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain types of lateral midfoot elastomeric networks, the first and second siloxanes can be present in a ratio from 1:99 to 20:80 by weight of the total silicone rubber. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, lateral midfoot elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

Forefoot Support Material

In some implementations, the forefoot support region, such as forefoot support region 104, includes a forefoot support material that includes a forefoot elastomeric network that can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the forefoot elastomeric network can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 4-7.5, 4-7, 4-6.5, 4-6, 4-5.5, 4-5, 4-4.5, 3.5-8, 3-8, or 2.5-8 MPa.

The forefoot elastomeric network can have an elasticity modulus (E) high stretch ratio of at least 6, 13, 20, 27, 34, 41, 48, 55, 62, 69, 76, 83, or 90 MPa, where any of the stated values can form an upper or lower endpoint of a range. The forefoot elastomeric network can have an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 27-90, 20-90, or 13-90 MPa.

The forefoot elastomeric network can have an ultimate tensile strength of at least 1, 2, 3, 4, 5, 6, 7, 8, 9, 10, 15, 20, or 25 MPa, where any of the stated values can form an upper or lower endpoint of a range. The forefoot elastomeric network can have an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10-25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the forefoot elastomeric network is a blend of at least one siloxane having a Shore hardness from 00-0 to 00-15 and a second siloxane having a Shore hardness from 10 A to 60 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain types of forefoot elastomeric networks, the first and second siloxanes can be present in a ratio from 1:99 to 20:80 by weight of the total silicone rubber. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, forefoot elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

As noted above, the forefoot support region may include one or more sub-regions. Such sub-regions of the forefoot support region include, but are not limited to, the lateral forefoot support region and the medial forefoot support region, and the medial forefoot support region may include a first metatarsal support region and a second metatarsal support region. For example, in the implementation shown in FIG. 5 described above, the forefoot support region 104 includes the lateral forefoot support region 104c, the first metatarsal support region 104a, and the second metatarsal support region 104b. The below description sets forth exemplary forefoot support materials used in each sub-region of the forefoot support region.

Medial Forefoot Support Material

In some implementations, the medial forefoot support region includes a medial forefoot support material that comprises a medial forefoot elastomeric network that can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the medial forefoot elastomeric network can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 4-7.5, 4-7, 4-6.5, 4-6, 4-5.5, 4-5, 4-4.5, 3.5-8, 3-8, or 2.5-8 MPa.

The medial forefoot elastomeric network can have an elasticity modulus (E) high stretch ratio of at least 6, 13, 20, 27, 34, 41, 48, 55, 62, 69, 76, 83, or 90 MPa, where any of the stated values can form an upper or lower endpoint of a range. The medial forefoot elastomeric network can have an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 27-90, 20-90, or 13-90 MPa.

The medial forefoot elastomeric network can have an ultimate tensile strength of at least 1, 2, 3, 4, 5, 6, 7, 8, 9, 10, 15, 20, or 25 MPa, where any of the stated values can form an upper or lower endpoint of a range. The medial forefoot elastomeric network can have an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10-25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the medial forefoot elastomeric network is a blend of at least one siloxane having a Shore hardness from 00-0 to 00-15 and a second siloxane having a Shore hardness from 10 A to 60 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain types of medial forefoot elastomeric networks, the first and second siloxanes can be present in a ratio from 1:99 to 20:80 by weight of the total silicone rubber. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, medial forefoot elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

First Metatarsal Support Material

In some implementations, the medial forefoot support region includes a first metatarsal support region, such as first metatarsal support region 104a. The first metatarsal support region includes a first metatarsal support material that comprises a first metatarsal elastomeric network that can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the first metatarsal elastomeric network can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 4-7.5, 4-7, 4-6.5, 4-6, 4-5.5, 4-5, 4-4.5, 3.5-8, 3-8, or 2.5-8 MPa.

The first metatarsal elastomeric network can have an elasticity modulus (E) high stretch ratio of at least 6, 13, 20, 27, 34, 41, 48, 55, 62, 69, 76, 83, or 90 MPa, where any of the stated values can form an upper or lower endpoint of a range. The first metatarsal elastomeric network can have an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 27-90, 20-90, or 13-90 MPa.

The first metatarsal elastomeric network can have an ultimate tensile strength of at least 1, 2, 3, 4, 5, 6, 7, 8, 9, 10, 15, 20, or 25 MPa, where any of the stated values can form an upper or lower endpoint of a range. The first metatarsal elastomeric network can have an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10-25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the first metatarsal elastomeric network is a blend of at least one siloxane having a Shore hardness from 00-0 to 00-15 and a second siloxane having a Shore hardness from 10 A to 40 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain types of first metatarsal elastomeric networks, the first and second siloxanes can be present in a ratio from 1:99 to 20:80 by weight of the total silicone rubber. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, first metatarsal elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

Second Metatarsal Support Material

In some implementations, the medial forefoot support region includes a second metatarsal support region, such as second metatarsal support region 104b. The second metatarsal support region includes a second metatarsal support material that comprises a second metatarsal elastomeric network that can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the second metatarsal elastomeric network can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 4-7.5, 4-7, 4-6.5, 4-6, 4-5.5, 4-5, 4-4.5, 3.5-8, 3-8, or 2.5-8 MPa.

The second metatarsal elastomeric network can have an elasticity modulus (E) high stretch ratio of at least 6, 13, 20, 27, 34, 41, 48, 55, 62, 69, 76, 83, or 90 MPa, where any of the stated values can form an upper or lower endpoint of a range. The second metatarsal elastomeric network can have an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 27-90, 20-90, or 13-90 MPa.

The second metatarsal elastomeric network can have an ultimate tensile strength of at least 1, 2, 3, 4, 5, 6, 7, 8, 9, 10, 15, 20, or 25 MPa, where any of the stated values can form an upper or lower endpoint of a range. The second metatarsal elastomeric network can have an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10-25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the second metatarsal elastomeric network is a blend of at least one siloxane having a Shore hardness from 00-0 to 00-15 and a second siloxane having a Shore hardness from 10 A to 40 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain types of second metatarsal elastomeric networks, the first and second siloxanes can be present in a ratio from 1:99 to 20:80 by weight of the total silicone rubber. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, second metatarsal elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

Lateral Forefoot Support Material

In some implementations, the lateral forefoot support region, such as lateral forefoot support region 104c, has a lateral forefoot support material that includes a lateral forefoot support elastomeric material. The lateral forefoot support elastomeric material can have an elasticity modulus (E) low stretch ratio of at least 2, 2.5, 3, 3.5, 4, 4.5, 5, 5.5, 6, 6.5, 7, 7.5, or 8 MPa, where any of the stated values can form an upper or lower endpoint of a range. In some implementations, the lateral forefoot support elastomeric material can have an elasticity modulus (E) low stretch ratio of no more than 8, 7.5, 7, 6.5, 6, 5.5, 5, 4.5, 4, 3.5, 3, 2.5, or 2 MPa, where any of the stated values can form an upper or lower endpoint of a range. For instance, the elasticity modulus (E) low stretch ratio can be from 2-8, 2-7.5, 2-7, 2-6.5, 2-6, 2-5.5, 2-5, 2-4.5, 2-4, 2-3.5, 2-3, 2-2.5, 7.5-8, 7-8, 6.5-8, 6-8, 5.5-8, 5-8, 4.5-8, 4-8, 4-7.5, 4-7, 4-6.5, 4-6, 4-5.5, 4-5, 4-4.5, 3.5-8, 3-8, or 2.5-8 MPa.

The lateral forefoot support elastomeric material can have an elasticity modulus (E) high stretch ratio of at least 6, 13, 20, 27, 34, 41, 48, 55, 62, 69, 76, 83, or 90 MPa, where any of the stated values can form an upper or lower endpoint of a range. The lateral forefoot support elastomeric material can have an elasticity modulus (E) high stretch ratio of no more than 90, 83, 76, 69, 62, 55, 48, 41, 34, 27, 20, 13 or 6 MPa, where any of the stated values can form an upper or lower endpoint of a range. For instance, the elasticity modulus (E) high stretch ratio can be from 6-90, 6-83, 6-76, 6-69, 6-62, 6-55, 6-48, 6-41, 6-34, 6-27, 6-20, 6-13, 83-90, 76-90, 69-90, 62-90, 55-90, 48-90, 41-90, 34-90, 34-83, 34-76, 34-69, 34-62, 34-55, 34-48, 34-41, 27-90, 20-90, or 13-90 MPa.

The lateral forefoot support elastomeric material can have an ultimate tensile strength of at least 1, 2, 3, 4, 5, 6, 7, 8, 9, 10, 15, 20, or 25 MPa, where any of the stated values can form an upper or lower endpoint of a range. The lateral forefoot support elastomeric material can have an ultimate tensile strength no greater than 25, 20, 15, 10, 9, 8, 7, 6, 5, 4, 3, 2, or 1 MPa, where any of the stated values can form an upper or lower endpoint of a range. The ultimate tensile strength can be from 1-25, 1-20, 1-15, 1-10, 1-9, 1-8, 1-7, 1-6, 1-5, 1-4, 1-3, 1-2, 20-25, 15-25, 10-25, 9-25, 8-25, 7-25, 6-25, 5-25, 4-25, 3-25, or 2-25 MPa. In some implementations, the ultimate tensile strength can be from 5-20, 5-15, 5-10, 10-15, 15-20, 15-25, or 20-25 MPa.

In some implementations, the lateral forefoot support elastomeric material is a blend of at least one siloxane having a Shore hardness from 00-0 to 00-15 and a second siloxane having a Shore hardness from 10 A to 60 A. In some implementations, the first siloxane has a Shore hardness from 00-05 to 00-15 and the second siloxane has a Shore hardness from 20 A to 40 A. In certain examples, the first siloxane has a Shore hardness of 00-10 and the second siloxane has a Shore hardness of 30 A.

For certain types of lateral forefoot elastomeric networks, the first and second siloxanes can be present in a ratio from 1:99 to 20:80 by weight of the total silicone rubber. When either the first or second siloxane is a two part silicone system, the ratio includes the sum of both Parts A and B. The first siloxane, having a Shore hardness from 00-05 to 00-15, can be present in an amount that is no more than 20%, 15%, 12%, 10%, 8%, 6%, 4%, or 2% by weight of the total silicone rubber content. The second siloxane, having a Shore hardness from 20 A to 40 A, can be present in an amount that is at least 80%, 85%, 88%, 90%, 92%, 94%, 96%, or 98% by weight of the total silicone rubber content.

In other examples, lateral forefoot elastomeric networks having a different spectrum of properties can be obtained by blending a first siloxane, having a Shore hardness from 00-05 to 00-15, in an amount that is at least 50%, 55%, 60%, 65%, 70%, 75%, or 80% by weight of the total silicone rubber content. The second siloxane, having a Shore hardness from 20 A to 40 A, can be present in an amount no more than 50, 45, 40, 35, 30, 25, or 20% by weight of the total silicone rubber content.

Other components can be incorporated into the support materials described above. For instance, oils can be added to modify the overall stiffness of the support materials, and dyes can be included to produce support materials of differing colors.

The skin simulant support materials can be prepared by combining one or more liquid siloxanes, as well as any additional ingredients, in a mold and allowing them to cure. Generally, all the siloxanes should be well blended to ensure a uniform simulant. In other implementations, however, a layered simulant can be prepared by sequentially curing different siloxane mixtures in a mold.

Figure 9:
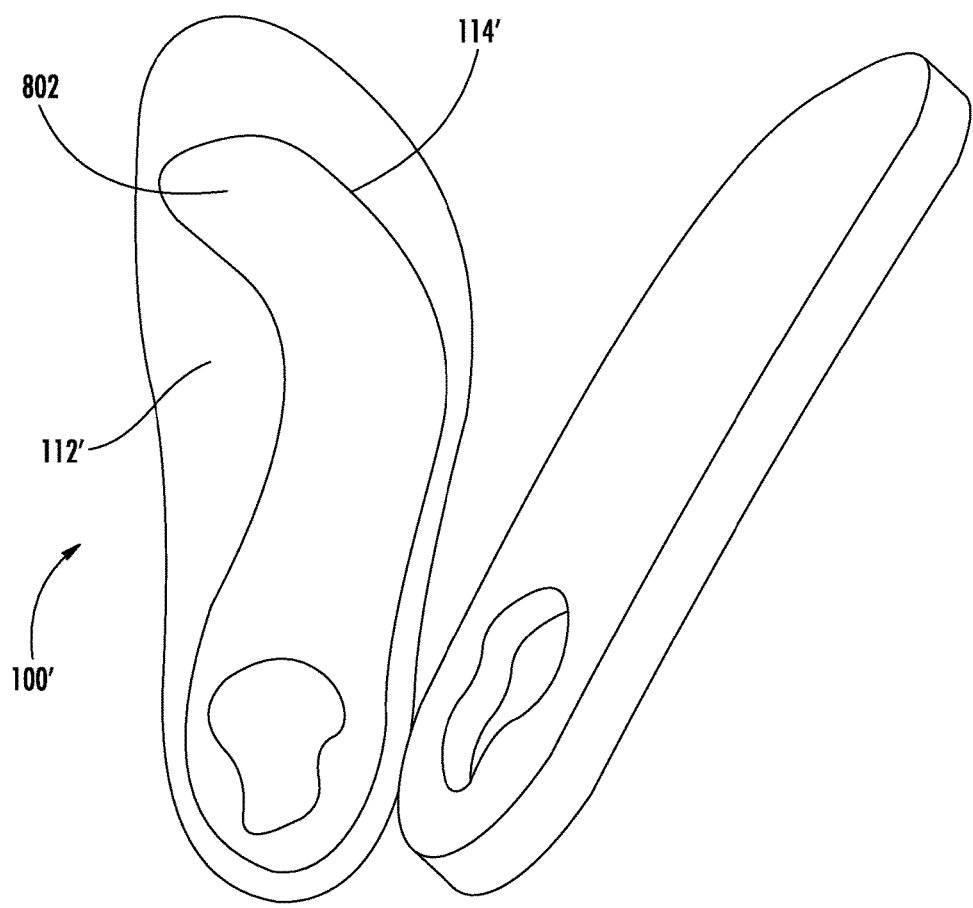
FIG. 9 illustrates a custom insole having an antimicrobial/sweat absorbent layer disposed in the recessed portion of the upper surface of the insole, according to various implementations.

The insoles disclosed herein can further include additional layers providing antimicrobial, order controlling, and/or sweat absorbing effects. The additional layer can include a thin fabric layer impregnated with antimicrobial liquids such as are known in the art. FIG. 9 illustrates an implementation of an insole 100' that includes an antimicrobial/sweat absorbent layer 802 disposed within the recessed portion 114' of the upper surface 112' of the insole 100'.

Method for Making Customized Insoles

Also disclosed herein are various implementations of methods of making the customized insoles described above. An exemplary process 800 according to one implementation is illustrated in FIG. 8. Method 800 begins by receiving image data of a plantar surface of a wearer's foot at step 802. In some examples, image data representing only a portion of the plantar surface of the wearer's foot is used, and in other examples, image data representing the full plantar surface of the wearer's foot is used. Also, the image data may be provided by one or more images of the plantar surface of the foot that are used separately or together. Images of the foot can be captured by a scanner, a pressure sensor, or other suitable imaging tool (e.g., a camera). In some implementations, the imaging tool may be part of a handheld computing device, such as a smart phone or tablet.

Figure 3:
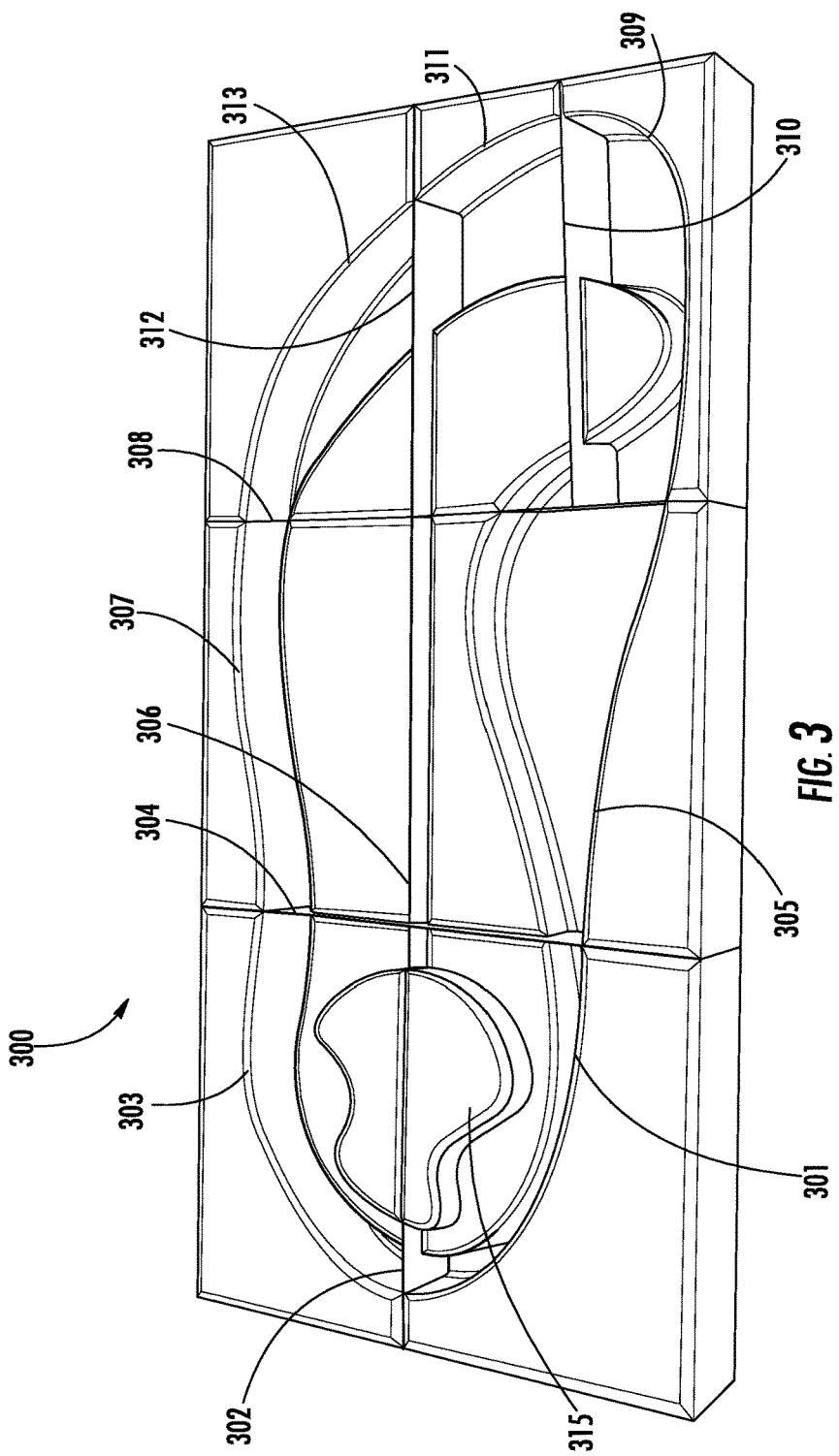
FIG. 3 illustrates an exemplary mold for a custom insole generated from data representative of a three dimensional model of the wearer's foot, according to one implementation.
Figure 10:
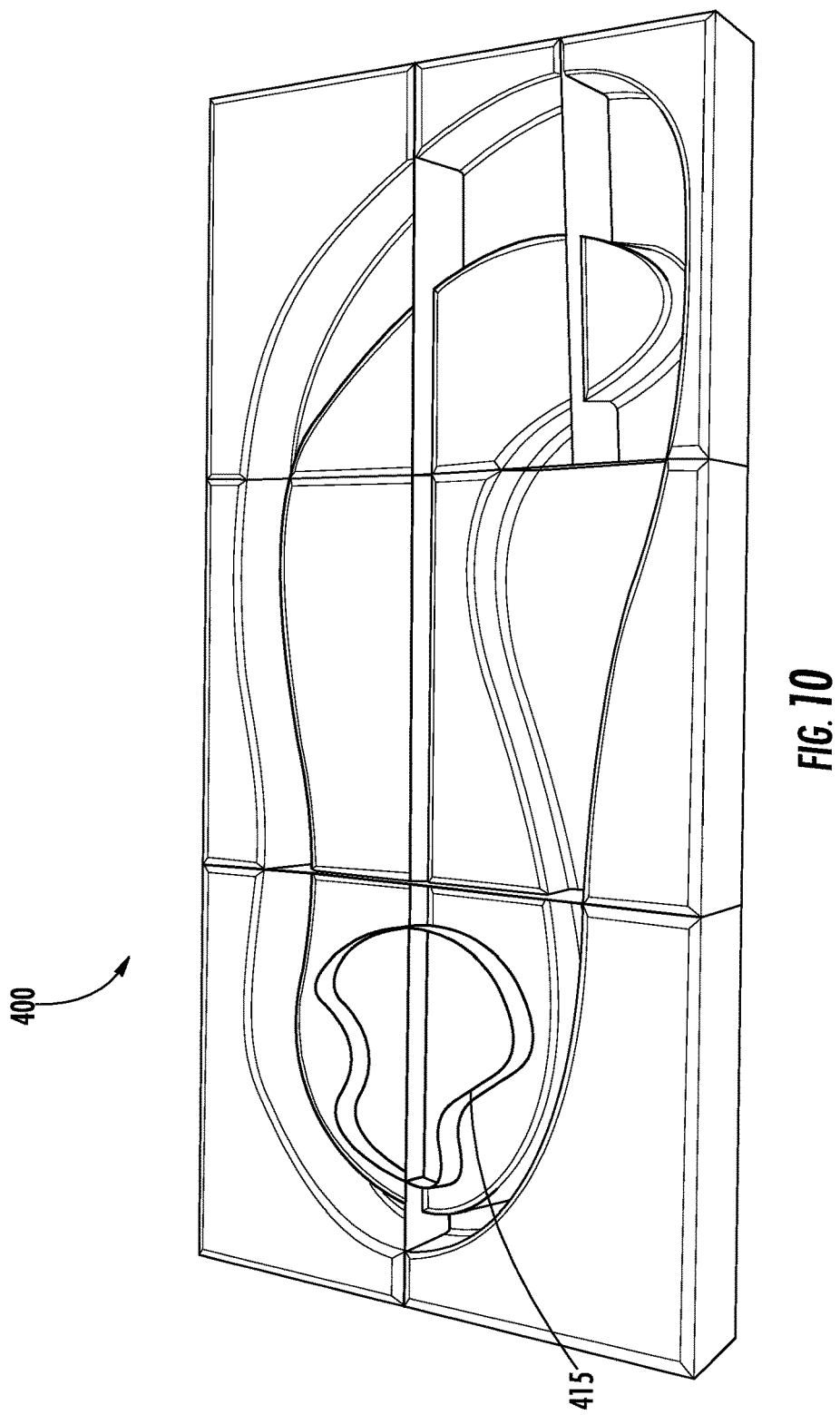
FIG. 10 illustrates an exemplary mold for a custom insole generated from data representative of a three dimensional model of the wearer's foot, according to another implementation.

As shown in step 804, data representative of a three dimensional model of at least a portion of the foot is generated using the image data received in step 802. For example, data representative of the 3D model of the portion of the foot may be generated using a computer aided designing (CAD) software, such as SOLIDWORKS. The data representative of the 3D model of the portion of the foot generated by the software may be based on dimensions and contours of the portion of the planter surface of the foot that are identified from the image data. In step 806, a standard insole size is selected based on the data representative of the three dimensional model of the portion of the foot generated in step 804. As shown in step 808, data representative of a three dimensional model of an insole and data representative of a three dimensional model of an inverse mold for forming the insole are generated based the data representative of the three dimensional model of the portion of the foot generated in step 804 and the standard insole size selected in step 806. The inverse mold is then formed in step 810 based on the data representative of the three dimensional model of the inverse mold from step 808. For example, the data representative of the three dimensional model of the insole and data representative of the three dimensional model of the inverse mold are generated with the CAD software. In addition, the contour of the insole and corresponding inverse mold can be adjusted to allow foot rest and cushioning at high pressure points on the insole and to adjust the plane in which one or more portions of the foot lie relative to the other portions of the foot. In addition, protrusions or isolation segment walls can be formed in the inverse mold where ulcer isolations segments are to be formed in the insole. In some implementations, the inverse mold is manufactured using additive manufacturing (e.g., 3D printing, such as a 3D printer from Ultimaker Inc.). FIGS. 3 and 10 illustrate exemplary inverse molds 300, 400.

In some implementations, the inverse mold can include one or more walls partitioning the mold into two or more regions that correspond to respective regions of the support layer 101. Each partitioned regions of the inverse mold can be filled with a selected precursor material, such as the siloxane precursor materials described above. The ratio of the first and second siloxanes for each region of the support layer 101 can be selected to provide the desired support to each of the various regions of the wearer's foot that are adjacent each support region of the insole in use. Examples of different regions of the inverse mold that can be partitioned with walls include, but are not limited to, a heel region, a midfoot region, and a forefoot region, which correspond to the heel support region, midfoot support region, and forefoot support region of the support layer of the insole described above. The heel and midfoot regions can each be further divided into lateral and medial regions that correspond to the lateral and medial support regions for each of the heel and midfoot support regions described above. And, the forefoot region can be divided into one or more metatarsal regions, such as the first metatarsal region, second metatarsal region, medial metatarsal region and/or lateral metatarsal region, which correspond to the first metatarsal support region, second metatarsal support region, medial metatarsal support region, and lateral metatarsal support regions described above.

For example, in the implementation shown in FIG. 3, the inverse mold 300 comprises a medial heel region 301, a lateral heel region 303, a medial midfoot region 305, a lateral midfoot region 307, a first metatarsal region 309, a second metatarsal region 311, a lateral metatarsal region 313, a heel region wall 302 that extends between the medial 301 and lateral heel regions 303, a midfoot region wall 306 that extends between the medial 305 and lateral 307 midfoot regions, a first metatarsal region wall 310 that extends between the first 309 and second metatarsal regions 311, a second metatarsal region wall 312 that extends between the second 311 and the lateral metatarsal regions 313, a first wall 304 that extends between the heel region wall 302 and the midfoot region wall 306 and between the heel regions 301, 303 and the midfoot regions 305, 307, and a second wall 308 that extends between the midfoot region wall 306 and the metatarsal region walls 310, 312 and between the midfoot regions 305, 307 and the metatarsal regions 309, 311, 313. In the implementation shown in FIG. 3, the first wall 304 and the second wall 308 are perpendicular to the walls 302, 306, 310, 312, but the walls may be arranged at other angles relative to each other.

If an ulcer or other skin injury is identified on the foot from the image data, a protrusion corresponding to the size, shape, location, and area of the skin injury can be formed as part of the inverse mold, which creates a hole or recess isolation segment in the support layer of the insole. For example, the outer perimeter of the protrusion is selected to be offset radially outwardly from the perimeter of the skin injury. In the implementation shown in FIG. 3, the protrusion 315 spans between portions of the medial heel region 301 and the lateral heel region 303.

In other implementations, such as shown in FIG. 10, the mold 400 can include one or more isolation segment walls 415 instead of the protrusion 315 shown in FIG. 3, and the isolation segment wall 415 defines a region into which a precursor material for siloxane can be poured. The precursor material poured into region 415 can have a softer Shore hardness that the precursor material poured into the region(s) adjacent the wall 415.

As shown in step 812, the insole is formed by pouring one or more selected precursor materials, such as the siloxane support materials described above, into the one or more regions of the inverse mold. For example, the precursor material selected for a particular region of the inverse mold can comprise either a single, one-part siloxane or a combination of two, two-part siloxanes, such as described above. In some examples, the precursor material comprises a first predetermined amount of a first, two-part siloxane (Part A) and a second predetermined amount of a second, two-part siloxane (Part B). The siloxane types and amounts for each precursor material are selected based on properties that support the respective portion of the plantar surface of the foot that is adjacent the insole in use. Thus, the selection of the precursor materials for each region is customizable for each wearer.

In implementations in which the isolation segment is formed by a protrusion in the inverse mold, the isolation segment is a hole or recess defined by the support layer of the insole. The isolation segment allows the support layer of the insole adjacent the isolation segment to support the tissue around the skin injury without contacting the skin injury. The isolation segment can be created to have various desired depths from the first surface of the support layer toward the second surface of the support layer, including creating an opening that extends through the support layer of the insole or partially through the support layer of the insole, by varying the size of the protrusion. The depth of the isolation segment may be selected depending on the severity of the skin injury. For example, more severe skin injuries may result in a deeper isolation segment to offload any direct stress on the injury and the possibility of stresses along the circumference of the injury.

The examples below are intended to further illustrate certain aspects of the methods and compounds described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Insole Preparation

As shown in FIG. 3, the insole mold 300 was divided into seven major foot regions (a medial heel region 301, a lateral heel region 303, a medial midfoot region 305, a lateral midfoot region 307, a first metatarsal region 309, a second metatarsal region 311, and a lateral metatarsal region 313). SOLIDWORKS software was used to create data representative of a three dimensional model of the user's foot and data representative of a three dimensional model of the inverse mold for the insole based on the data representative of the three dimensional model of the user's foot. The data representative of the three dimensional model of the inverse mold was used to print the inverse mold using additive manufacturing (e.g., using polylactic acid (PLA) filament), as shown in FIG. 3. Multiple skin-like materials (with the same or different stiffness properties), such as those described above, were poured into regions periodically (e.g., at 1 hour intervals) to allow the materials to blend in well and to provide strong adhesion between the materials in adjacent support regions. The materials may also be layered within a region, according to some implementations.

FIG. 5 illustrates an implementation of insole 100 formed in the mold 300 shown in FIG. 3. Five different materials were selected for pouring into the regions 301, 303, 305, 307, 309, 311, 313 of the inverse mold 300. In particular, a first material was selected for pouring into the first metatarsal region 309 for forming the first metatarsal support region 104a of the insole 100, a second material was selected for pouring into the second metatarsal region 311 and the lateral metatarsal region 313 for forming the second metatarsal support region 104b and the lateral metatarsal region 104c of the insole 100, a third material was selected for pouring into the medial midfoot region 305 for forming the medial midfoot support region 106a of the insole 100, a fourth material was selected for pouring into the lateral midfoot region 307 for forming the lateral midfoot support region 106b of the insole 100, and a fifth material was selected for pouring into the medial heel region 301 and the lateral heel region 303 for forming the heel support region 107 of the insole 100. In addition, the protrusion 315 formed the recess 108 in the heel support region 107.

Example 2: Additional Insole Designs with Custom Isolation Segment

FIGS. 6 and 7 illustrate additional examples of custom insoles 600, 700, respectively, that include differently shaped support regions and support materials for each support region. In particular, the insole 600 shown in FIG. 6 includes base layer 610 and support layer 601, and the support layer 601 includes forefoot support region 604, medial midfoot support region 606a, lateral midfoot support region 606b, and heel support region 607. The material of the base layer 610 is harder than the materials of the support layer 601. The isolation segment 608 is defined in the heel support region 607. In use, the forefoot support region 604 supports the hallux portion 22, the second toe portion 26, the lateral toe portion 30, the lateral metatarsal portion 28, and portion of the second metatarsal portion 24 of the wearer's foot 10. The medial midfoot support region 606a supports the first metatarsal portion 20, a portion of the second metatarsal portion 22, and a portion of the medial midfoot portion 16 of the wearer's foot 10. The lateral midfoot support region 606b supports the lateral midfoot portion 18 and a portion of the medial midfoot portion 16 of the wearer's foot 10. And, the heel support region 607 supports the medial 12 and lateral 14 heel portions of the wearer's foot 10. The isolation segment 608 supports a skin injury on the heel portion of the wearer's foot.

The exemplary custom insole 700 shown in FIG. 7 is similar to the insole 600 described in relation to FIG. 6 except that the isolation segment 708 is defined in a forefoot support region 704 of the insole 700 to support a skin injury on the lateral metatarsal portion of the wearer's foot 10. The insole 700 further includes a medial midfoot support region 706a, a lateral midfoot support region 706b, and a heel support region 707.

The materials in each support regions may be made of different variants of skin simulants (corresponding to different silicone combinations) with varying stiffnesses. The isolation segments may be of any geometry and size and defined in any region of the support layer of the insole.

The methods and compositions of the appended claims are not limited in scope by the specific methods and compositions described herein, which are intended as illustrations of a few aspects of the claims and any methods and compositions that are functionally equivalent are within the scope of this disclosure. Various modifications of the methods and compositions in addition to those shown and described herein are intended to fall within the scope of the appended claims. Further, while only certain representative methods, compositions, and aspects of these methods and compositions are specifically described, other methods and compositions and combinations of various features of the methods and compositions are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. An insole having a support layer, the support layer comprising one or more support regions, each support region comprising a support material simulating biomechanical properties of human skin, the support material comprising an elastomeric network having an elasticity modulus low stretch ratio from 2-8 MPa and an elasticity modulus high stretch ratio from 6-90 MPa, wherein the elasticity modulus high stretch ratio is greater than the elasticity modulus low stretch ratio.

2. The insole of claim 1, wherein the elastomeric network comprises a crosslinked siloxane network comprising a first siloxane having a Shore Hardness of from 00-0 to 00-15 and a second siloxane having a Shore Hardness of from 10 A to 60 A.

3. The insole of claim 2, wherein the first siloxane is present in an amount that is no more than 20% by weight relative to the total weight of the elastomeric network, and the second siloxane is present in an amount that is at least 80% by weight relative to the total weight of the elastomeric network.

4. An insole having a support layer, the support layer comprising a heel support region, the heel support region comprising a heel support material simulating biomechanical properties of human skin, the heel support material comprising a heel elastomeric network having an elasticity modulus low stretch ratio from 2-8 MPa and an elasticity modulus high stretch ratio from 6-90 MPa, wherein the elasticity modulus high stretch ratio is greater than the elasticity modulus low stretch ratio.

5. The insole of claim 4, wherein the heel elastomeric network comprises a crosslinked siloxane network comprising a first heel siloxane having a Shore Hardness of from 00-0 to 00-15 and a second heel siloxane having a Shore Hardness of from 10 A to 60 A.

6. The insole of claim 5, wherein the first heel siloxane is present in an amount that is no more than 20% by weight relative to the total weight of the heel elastomeric network, and the second heel siloxane is present in an amount that is at least 80% by weight relative to the total weight of the heel elastomeric network.

7. The insole of claim 4, wherein the support layer further comprises a midfoot support region, the midfoot support region comprising a midfoot support material simulating biomechanical properties of human skin, the midfoot support material comprising a midfoot elastomeric network having an elasticity modulus low stretch ratio from 2-8 MPa and an elasticity modulus high stretch ratio from 6-90 MPa, wherein the elasticity modulus high stretch ratio of the midfoot elastomeric network is greater than the elasticity modulus low stretch ratio of the midfoot elastomeric network.

8. The insole of claim 7, wherein the midfoot elastomeric network comprises a crosslinked siloxane network comprising a first midfoot siloxane having a Shore Hardness of from 00-0 to 00-15 and a second midfoot siloxane having a Shore Hardness of from 10 A to 60 A.

9. The insole of claim 8, wherein the first midfoot siloxane is present in an amount that is no more than 20% by weight relative to the total weight of the midfoot elastomeric network, and the second midfoot siloxane is present in an amount from that is at least 80% by weight relative to the total weight of the midfoot elastomeric network.

10. The insole of claim 7, wherein the support layer further comprises a forefoot support region, the forefoot support region comprising a forefoot support material simulating biomechanical properties of human skin, the forefoot support material comprising a forefoot elastomeric network having an elasticity modulus low stretch ratio from 2-8 MPa, and an elasticity modulus high stretch ratio from 6-90 MPa wherein the elasticity modulus high stretch ratio of the forefoot elastomeric network is greater than the elasticity modulus low stretch ratio of the forefoot elastomeric network.

11. The insole of claim 10, wherein the forefoot elastomeric network comprises a crosslinked siloxane network comprising a first forefoot siloxane having a Shore Hardness of from 00-0 to 00-15 and a second forefoot siloxane having a Shore Hardness of from 10 A to 60 A.

12. The insole of claim 11, wherein the first forefoot siloxane is present in an amount from that is no more than 20% by weight relative to the total weight of the forefoot elastomeric network, and the second forefoot siloxane is present in an amount from that is at least 80% by weight relative to the total weight of the forefoot elastomeric network.

13. The insole of claim 10, wherein a first surface of the support layer is configured for facing a plantar surface of a user's foot, and the first surface defines a recessed portion.

14. The insole of claim 13, wherein the recessed portion is arranged to receive one or more lateral portions of the user's foot.

15. The insole of claim 14, wherein the recessed portion extends between the lateral midfoot support region and the lateral heel support region of the support layer.

16. The insole of claim 15, wherein the recessed portion further extends into at least a portion of the forefoot support region.

17. The insole of claim 13, wherein the recessed portion is arranged to receive one or more medial portions of the user's foot.

18. The insole of claim 13, further comprising a sweat absorbent material disposed at least within the recessed portion.

19. The insole of claim 13, further comprising an anti-microbial material disposed at least within the recessed portion.

20. The insole of claim 13, wherein a second surface of the support layer is opposite and spaced apart from the first surface of the support layer, the insole further comprising a base layer coupled to the second surface of the support layer.

21. The insole of claim 10, wherein at least one region of the support layer defines an isolation segment that defines a recess, the recess extends through a first surface of the support layer toward a second surface of the support layer that is opposite and spaced apart from the first surface, the isolation segment having a perimeter that corresponds to a perimeter of a skin injury on a plantar surface of a user's foot, wherein the first surface faces the plantar surface of the user's foot in use.

22. The insole of claim 10, wherein at least one support region of the support layer defines an isolation segment, the isolation segment comprising an isolation segment siloxane having a Shore hardness that is less than the Shore hardness of the siloxane in the at least one support region defining the isolation segment.

* * * * *